United States Patent [19]

Fischer

[11] Patent Number: 4,677,856
[45] Date of Patent: Jul. 7, 1987

[54] GUIDED-BEND TEST APPARATUS

[76] Inventor: Glenn N. Fischer, c/o Fischer Engineering Company 7595 E. Singer Rd., Dayton, Ohio 45424

[21] Appl. No.: 851,199

[22] Filed: Apr. 14, 1986

[51] Int. Cl.$^4$ .............................................. G01N 3/20
[52] U.S. Cl. .................................................... 73/850
[58] Field of Search ................ 73/849, 850, 851, 852, 73/854

[56] References Cited

U.S. PATENT DOCUMENTS

| 2,676,381 | 4/1954 | Holmes | 73/859 |
| 3,142,174 | 7/1964 | Baker | 73/852 |
| 3,500,679 | 3/1970 | Smith | 73/850 |
| 4,573,360 | 3/1986 | Yoneda | 73/850 |

FOREIGN PATENT DOCUMENTS

| 0920942 | 12/1954 | Fed. Rep. of Germany | 73/850 |
| 0805113 | 2/1981 | U.S.S.R. | 73/850 |

Primary Examiner—Stewart J. Levy
Assistant Examiner—Robert R. Raevis
Attorney, Agent, or Firm—Biebel, French & Nauman

[57] ABSTRACT

Apparatus for testing the ductility of a weld located within an elongated specimen is used with a separate apparatus having a lowerable ram. The apparatus includes a base defining a support surface having a central opening. Each roller of a pair has a width sufficient for supporting the test specimen, and is connected to the base to extend over the opening. A beam located above the base is guided for movement toward and away from the support surface, and is biased upwardly into a raised position over the surface. A mandrel extends downwardly from the beam, defining at its end a working surface. When the beam is in its raised position, the mandrel is located with the working surface above but between the rollers. The specimen may be positioned on the rollers with the weld disposed between the rollers. The mandrel is forced downwardly by the ram, with the mandrel contacting the specimen along the working surface to bend the specimen into the opening. The bending process exhibits the ductility of the weld as well as the presence of any defects in the weld.

11 Claims, 8 Drawing Figures

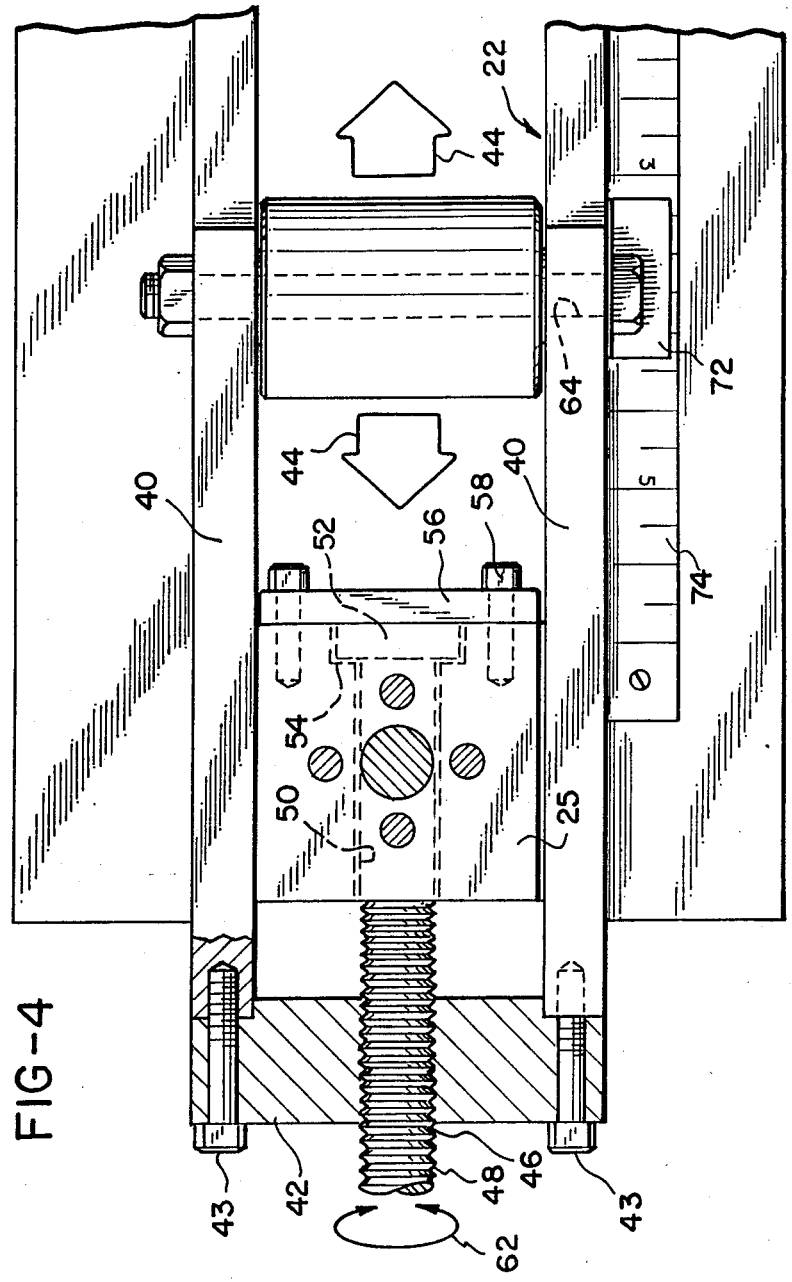

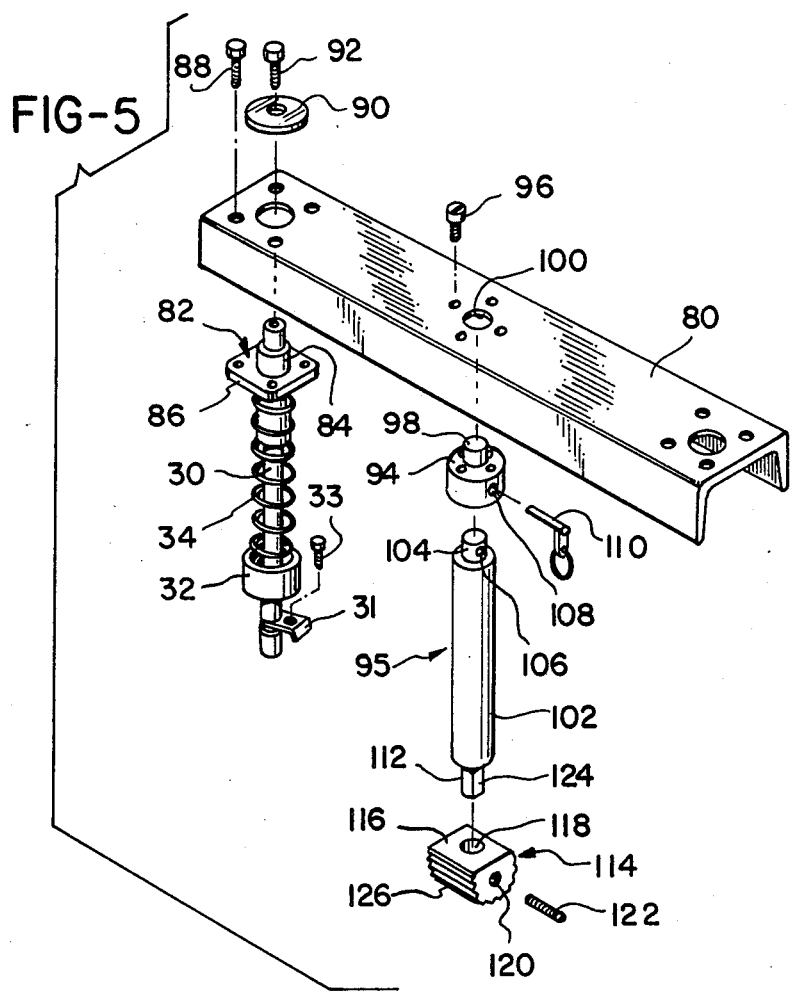
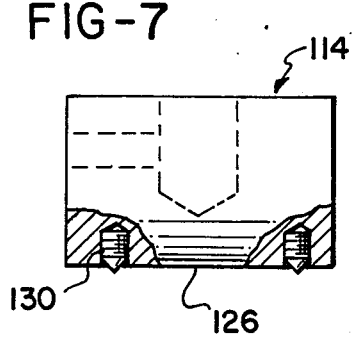
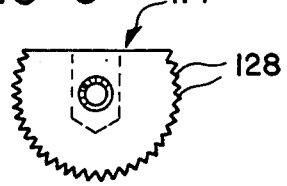
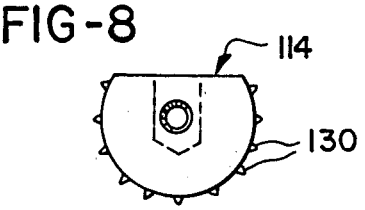

GUIDED-BEND TEST APPARATUS

BACKGROUND OF THE INVENTION

The present invention relates generally to an apparatus used in performing tests to determine the ductility of welds. Specifically, the test is carried out using the apparatus to operate upon a metallic weld test specimen by subjecting the specimen, in the vicinity of the weld, to a bending force.

It is frequently desirable or necessary to test the ductility of a weld joining two pieces of similar or dissimilar metallic materials. For example, as a product is being designed that will require welding for its assembly, the charateristics and performance of particular materials and welding techniques may be tested to ensure that they possess adequate ductility in conformance with applicable codes or standards. Failure to possess such ductility may result in a weld which can fracture when subjected to stresses or strains. As another example, training an individual in welding techniques or determining the individual's welding skill can be facilitated by testing the ductility of welds made.

The guided bend test has been widely used in the welding industry for the purposes noted above. A number of professional societies, such as the American Society of Mechanical Engineers, have defined standards for the uniform application of this test. In performing the test, a sample is made by welding two plates or two lengths of pipe together in end-to-end fashion. Single bar specimens are cut from the sample in such a way that the weld is either transverse or longitudinal to the length of the specimen. Each test specimen is supported at two points, with the weld positioned equidistantly between the support points. A ram having a curved working surface is moved into contact with the specimen at the weld, and is forced against the specimen, causing it to bend. The extent to which the specimen may be bent without breaking along the weld is indicative of the weld ductility. The presence of defects in the weld may also be exhibited by such a bend test.

A known test device for performing the guided bend test is shown in U.S. Pat. No. 3,500,679 issued Mar. 17, 1970 to Smith. The device includes a base having means for supporting the specimen at either end with the weld left unsupported. A hydraulic jack is mounted on the base, with a ram having a curved working surface being located for upward movement against the weld. A pair of rollers are positioned to be located above the specimen, so that the ram forces the specimen against the rollers in a manner that bends the specimen to drive it between the rollers.

The Smith device posesses several disadvantages. The lifting motion of the ram against the specimen from beneath the specimen causes difficulties in balancing the specimen such that bending force can be evenly applied. Further, the Smith device is relatively lightweight, making it inadequate for larger specimens.

A further problem experienced with apparatus such as the Smith device is slippage of the specimen about the ram periphery. This may occur if the thickness of the weld is different from that of the base metal or the weld metal is less ductile than the base metal. Slippage can also occur if the specimens are relatively thin.

Bend testing is not usually a continuous operation, and is normally performed only occasionally. Most manufacturing, fabricating and testing companies already own powered actuating equipment which could be used to provide the motive power needed to perform bend tests. Moreover, many smaller shops which rely upon welding would be benefited by possessing the necessary apparatus to carry out the guided bend weld test. However, because the test device represents an additional piece of powered, operating equipment, it is financially difficult for many of these establishments to justify the acquisition of such a piece of equipment. Consequently, the test must either be done without or performed by an outside contractor.

What is needed, therefore, is an apparatus for use in bend testing which is portable and capable of operating in conjunction with existing power equipment, e.g., hydraulic shop presses or tensile testing machines, which are intended for multipurpose use. The apparatus should include a means of support for the specimen which will aid in alignment and centering of the weld with respect to the ram. Further, the apparatus must be capable of handling specimens of varying sizes. The apparatus must also include means for solving the problem of specimen slippage around the ram. Such an apparatus will enable many more establishments to have access to the necessary equipment for performing bend testing. Moreover, despite relatively inexpensive construction, the apparatus must be sufficiently rugged to withstand the forces generated during performance of the test.

SUMMARY OF THE INVENTION

The present invention provides an apparatus for testing the ductility of a weld specimen taken from a sample formed by two plates or pipes connected in end-to-end fashion. The apparatus is designed for use with a separate apparatus having a ram supported for raising and lowering over a bed. Thus, the present invention takes advantage of the recognition that the most complex and costly component of a guided-bend test device is the ram used to exert force upon the specimen and the mechanism for driving and retracting the ram.

The apparatus includes a base defining a support surface having a central opening. A pair of rollers is provided, with each roller having a pair of ends and a width sufficient for supporting the specimen. Each roller is connected at its ends to the base so as to extend over the opening. A beam is located above the support surface of the base and means is provided for guiding the beam for movement toward and away from the support surface. The beam is biased upwardly into a raised position over the support surface. A downwardly extending mandrel is connected to the beam, and defines at its end a working surface. The mandrel is located, when the beam is in its raised position, with the working surface above but between the rollers. The specimen may be positioned upon the rollers with the weld disposed equidistant between the rollers. The mandrel is then forced downwardly by the ram to cause the mandrel to contact the specimen along the working surface, so as to bend the specimen into the opening.

Each of the rollers may be connected to the base by means for releasably connecting the roller. Further, additonal pairs of rollers having a variety of diameters may be provided, with the pairs of rollers being selectively interchangeable.

The apparatus may also include means for selectively moving the rollers of the pair toward and away from each other while supporting the rollers on the base. This selective moving means can include two pairs of members, each of the members disposed in parallel with the other members of the pair for sliding movement along the upper base surface, the pairs of members being disposed at opposite ends of the frame. Each of the rollers is connected at its ends between the members of one of the pairs.

The selective moving means may further include a vise block secured to each end of the frame, with a screw shaft connected to each vise block for non-threaded rotation. A plate defines a threaded bore engaged with the screw shaft, the plate further being connected to said members of the pair of members, whereby rotation of the shaft causes sliding movement of the members along the upper surface.

The mandrel may include a mandrel body and a bottom portion attached thereto, the working surface of the mandrel being defined on the bottom portion. The working surface may further define a curved, circular surface having a radius.

The working surface may be a roughened surface. This roughened surface can be formed by knurling. Alternatively, the roughened surface can be defined by a plurality of pins embedded in the working surface.

Accordingly, it is an object of the present invention to provide an apparatus for use in performing the guided bend weld test that does not require its own source of power for applying bending force to a specimen; to provide such an apparatus for use in bend testing which is portable and capable of operating in conjunction with existing power equipment intended for multipurpose use; to provide such an apparatus including means for supporting the specimen which will aid in alignment and centering of the weld with respect to the ram; to provide such an apparatus that is capable of use with various sizes of test specimens; to provide such an apparatus for solving the problem of specimen slippage around the ram; and to provide such an apparatus that is sufficiently rugged to withstand the forces generated during performance of the bend test.

Other objects and advantages of the present invention will be apparent from the following description, the accompanying drawings, and the appended claims.

BRIEF DESCRIPTION OF THE DRAWINGS

FIG. 5 is a perspective, exploded view of the upper portion of the fixtue of FIG. 1, with one of the upright posts and associated parts omitted;

FIG. 6 is a end view of an end member for the mandrel of the apparatus;

FIG. 7 is a side view of an alternative embodiment for the mandrel end member; and FIG. 8 is an end view of the member shown in FIG. 7.

DETAILED DESCRIPTION OF THE PREFERRED EMBODIMENT

Figure 1:
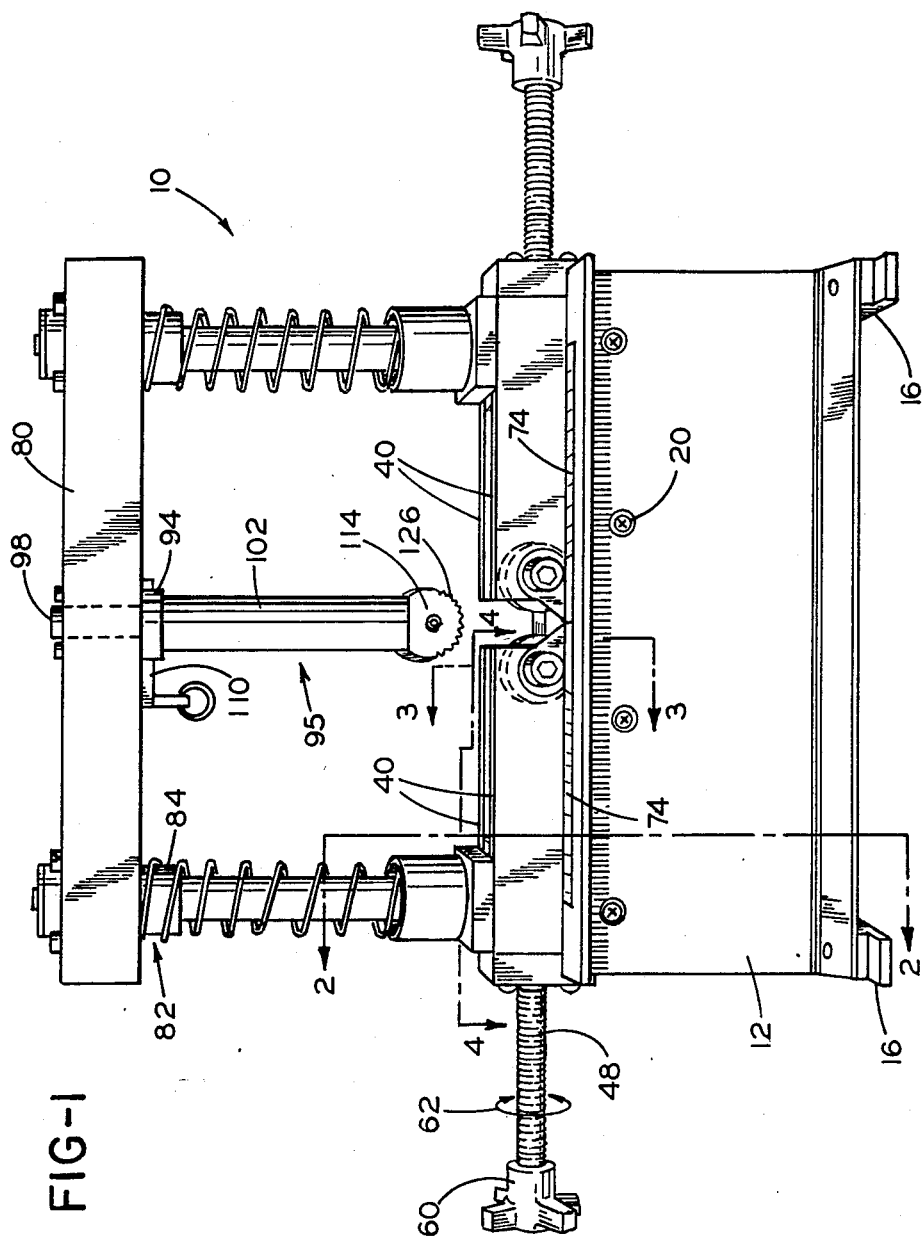
FIG. 1 is a front perspective view of a guided-bend test apparatus in accordance with the present invention.
Figure 2:
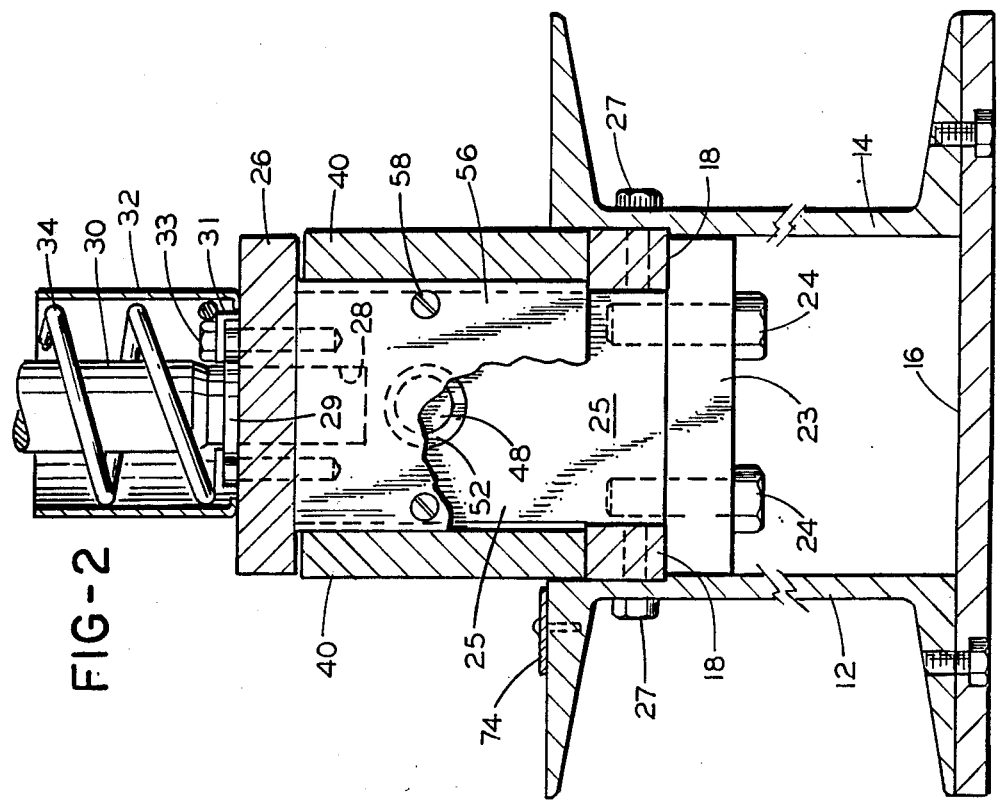
FIG. 2 is a sectional view of the lower portion of the apparatus, taken generally along line 2—2 of FIG. 1.

Referring generally to FIGS. 1 and 2, an apparatus 10 is shown for use with a separate apparatus (not shown) having a ram that is capable of being raised and lowered away from and toward a bed. Such an apparatus may be a hydraulic press or a tensile/compression testing machine. Other appropriate types of apparatus capable of generating sufficient downward force may also be used.

The apparatus 10 must be sufficiently rigid to withstand forces that are exerted upon it, as will be explained in detail below, by the force-providing apparatus. Thus, the various components of the apparatus 10 are formed from a rigid material, preferably a metallic material, and most preferably steel.

The apparatus 10 includes forward and rearward frame portions 12 and 14, respectively. These portions may be lengths of relatively shallow U-shaped channel. Frame portions 12 and 14 are connected at their lower ends by a pair of cross members 16. Inner slide rails 18 are connected by bolts 20 between portions 12 and 14 near, but slightly below, their upper ends. Rails 18 extend the full length of frame portions 12 and 14. Thus, rails 18 together define an upper work surface for the apparatus base, and in fact may be considered as part of the base. As seen also by reference to FIG. 4, the space between rails 18 is open, whereby a central opening 22 is formed, opening into the central region between frame portions 12 and 14.

A pair of blocks 25 (see FIG. 2) is mounted between rails 18 at each end of the rails, secured by bolts 27 passing through frame portions 12 and 14 and rails 18. A lower plate 23 is connected by bolts 24 to the bottom surface of each block 25. A retaining plate 26 is in turn secured to the top surface of each block 25.

A circular bore 28 is formed through each plate 26 and extends partially into each block 25. An upwardly extending cylindrical post 30 is fittable within each bore 28. A flange 29 is formed near the lower end of post 30, so that the flange is located against plate 26 when post 30 is positioned into bore 28. Clips 31 and bolts 33 cooperate with flange 29 to secure post 30 and plate 26 to block 25. A retaining cup 32 is positioned on the upper surface of plate 26, and a coil spring 34 is placed over post 30, with its lower end contained within cup 32.

Two pairs of parallel slide members 40 are positioned on inner slide rails 18, with one pair of slide members 40 located at each end of the apparatus 10. As best shown in FIG. 4, wherein only one half of the apparatus is shown (the opposite half being identical), each slide member 40 of the pair is located on one rail 18 adjacent to one of the frame portions 12 and 14. At the outer end of apparatus 10, the members 40 of each pair are connected by an end plate 42 attached to members 40 by screws 43.

Referring to FIG. 2, members 40 are of a width sufficient to fit between frame portions 12 and 14 and block 25. Further, each member 40 is of a height sufficient to fit between rail 18 and retaining plate 26. Each sliding member is further sized to fit closely within the boundaries defined by inner rail 18, frame portion 12 or 14, block 25 and plate 26, but is not fitted particularly snugly into this area. Thus, each pair of members 40 may be slidably moved in a lateral direction along rails 18, as indicated by arrows 44 in FIG. 4.

Continuing to refer to FIG. 4, a threaded bore 46 is formed through the center of each connecting plate 42, and a threaded shaft 48 is engaged with threaded bore 46. A smooth bore 50 is formed through block 25, having a diameter slightly greater than that of shaft 48. A nut 52 is welded or otherwise attached to the end of shaft 48, and bore 50 is provided with a widened portion 54 into which nut 52 is fittable. Nut 52 and portion 54 thus cooperate to secure shaft 48 from movement outwardly with respect to block 25. A plate 56 is attached to block 25 by screws 58, thereby securing shaft 48 from movement in the opposite direction.

An appropriate handle 60 (FIG. 1) is fixedly connected to the outer end of shaft 48, whereby an operator of apparatus 10 may grip handle 60 for rotation of shaft 48 in either direction, as indicated by arrow 62. This will result in movement of sliding members 40 either inwardly or outwardly with respect to apparatus 10.

Figure 3:
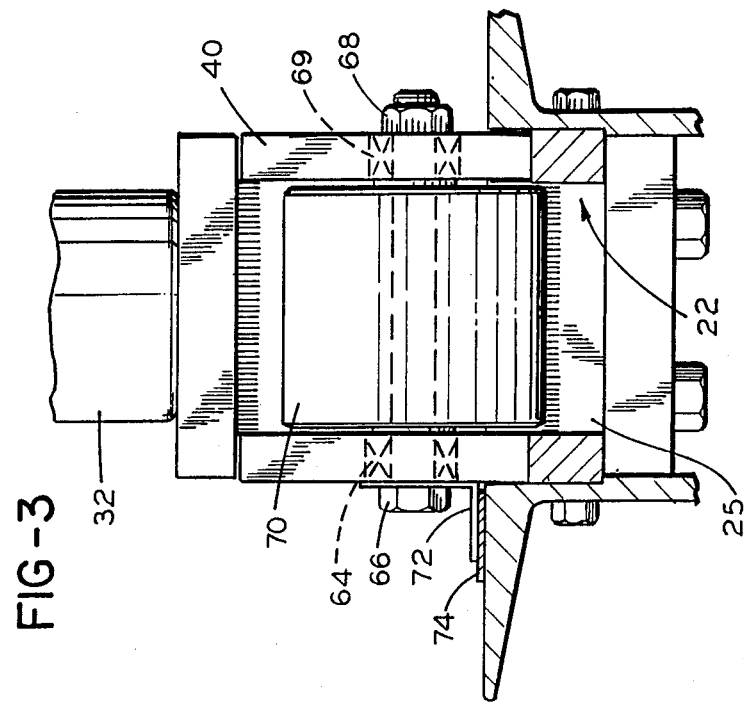
FIG. 3 is an additional sectional view of the lower portion of the apparatus, taken generally along line 3—3 of FIG. 4 is a top plan view of approximately one half of the lower portion of the apparatus, taken generally along line 4—4 of FIG. 1.

As best seen in FIGS. 3 and 4, each sliding member 40 of each pair is provided, at its end opposite from plate 42, with a transverse bore 64. A bolt 66 is passed through each bore 64 of the pair of sliding members 40, and is secured by nut 68. Bolt 66 thus defines a shaft on which are supported bearings 69 and a cylindrical roller 70 which extends between the sliding members 40. Bolt 66 and nut 68 are provided for relatively easy removal, so that roller 70 may be removed and relatively easily interchanged for a different roller, for reasons that will be explained in more detail below.

An angle piece 72 is secured against the outer surface of one sliding member by bolt 66. A ruled scale 74 is secured to the top surface of frame portion 12, so that angle piece 72 is positioned on top of scale 74. Thus, angle piece 72 serves as a marker for scale 74, with its leading edge indicating the position of the forwardmost portions of rollers 70 relative to each other and to frame portions 12 and 14.

Referring now to FIGS. 1 and 5, each post 30 extends upwardly from block 25 toward one end of a cross beam 80 having a length substantially identical to that of frame portions 12 and 14. (It will be recognized that one post 30 and parts associated therewith is omitted from FIG. 5, but is identical to the post 30 shown.) A guide collar 82 includes a tubular portion 84 and an outwardly extending flange 86. Portion 84 has a central opening that is slightly larger than the diameter of post 30, and includes nylon bushings, so that collar 82 is slidable along post 30. Spring 34, which is located on post 30, fits around the exterior of portion 84, with the upper end of spring 34 abutting against flange 86.

Flange 86 of collar 82 is connected to beam 80 by a plurality of bolts 88. Because collar 82 is slidable along post 30, this results in beam 80 being similarly capable of relative movement along posts 30. A washer 90 having a diameter larger than the inner diameter of tube portion 84 is secured by bolt 92 to the top of each post 30. Thus, while spring 34 normally urges collar 82 and beam 80 upwardly along post 30, washer 90 acts as an upward stop.

A mandrel retainer 94 is secured to the lower surface of beam 80 by a plurality of bolts 96. An upward knob 98 carried on retainer 94 extends through an opening 100 in beam 80.

An elongated mandrel body 102 defines the largest portion of downwardly extending mandrel 95. Body 102 includes an upper portion 104 having an opening 106 defined therein. Portion 104 is fittable into an opening (not shown) in the lower surface of mandrel retainer 94 so that bore 106 aligns with a similar bore 108 formed in retainer 94. A pin 110 may be inserted through bores 106 and 108 to secure mandrel body 102 to retainer 94 and, in turn, to beam 80. Other alternative attaching means, such as a threaded screw, may be used to secure body 102 to retainer 94.

A narrowed portion 112 is located at the lower end of mandrel body 102. An end member 114 defines an upper surface 116 having a bore 118 formed therein. Portion 112 of body 102 is fittable within bore 118. A second, threaded bore 120 is formed extending inwardly from a side surface of member 114, intersecting bore 118. A threaded set screw 122 is fittable within bore 120, and engages an indented portion 24 defined at the lower end of portion 112 of body 102. Thus, member 114 may be secured to the lower end of mandrel body 102.

Member 114 defines a curved, substantially cylindrical working surface 126. One common problem with weld testing apparatus has been a tendency of the specimen to slip with respect to the mandrel as bending force is being applied. Accordingly, surface 126 is provided with a series of knurls 128. An alternative to knurling this surface is shown in FIGS. 7 and 8. Pointed pins 130 are embedded into the working surface 126 of member 114. Pins 130 are shown in FIG. 7 as being secured by the provision of threads. However, it will be recognized that other methods of securing pins 130 may be appropriate, including welding, attaching with set screws, force fitting, or even cementing. Further, it should be recognized that still other alternatives for providing a roughened working surface 126 may be employed.

The operation of the apparatus 10 will now be described with reference to FIG. 1. A specimen to be tested (not shown) is formed by welding two plates or two lengths of pipe together in end-to-end fashion in accordance with the techniques to be tested. Single bar specimens are cut from the sample in such a way that the weld is either transverse or longitudinal to the length of the specimen.

In accordance with industry standards, the radius dimensions of rollers 70 and of the circular working surface of member 114, along with the relative spacing between rollers 70, are all determined by the dimensions of the sample to be tested. Fixture 10 is therefore supplied with a variety of sizes of roller pairs 70 and members 114. The proper size of member 114 is selected upon the basis of the specimen thickness and material.

Rollers 70 are installed by removing bolts 66 and nuts 68. The proper rollers are installed by replacing the bolts and nuts. Member 114 is most easily changed by releasing pin 110 and removing mandrel body 102 from apparatus 10. Set screw 122 is then manipulated to detach member 114 from body 102. The appropriately sized member 114 is installed, and mandrel body 102 is reattached by pin 110 to apparatus 10. Finally, the proper spacing between rollers 70 is achieved by manipulating handles 60 located at each end of the shafts 48, thereby moving rollers 70 either inwardly or outwardly. By referring to scales 74, the proper dimensions may be readily achieved.

Because apparatus 10 is not provided with its own source of driving force for lowering mandrel 95, it is necessary that apparatus 10 be used in conjunction with some means of providing such force. This is in fact an advantage, as most locations where such a test would be performed are likely to have an appropriate driving mechanism. Thus, it is not necessary that a more expensive and complex piece of equipment be purchased.

The apparatus 10 is positioned within the outside mechanism which may be, for example, a hydraulically driven mechanical press, such that the press ram contacts knob 98 extending through the top of beam 80.

The specimen is then positioned on rollers 70, with the weld located equidistantly between the rollers. The ram of the external mechanism is placed in contact with and applies force to knob 98 of member 94, thereby transmitting a downward driving force to member 114, which in turn contacts the specimen. Further application of force drives member 114 against the specimen, causing it to bend downwardly between rollers 70. Force is continuously applied until the specimen is formed into a complete 180° bend and is ejected between frame portions 12 and 14, or until such time as the weld fractures, whereupon the specimen pieces will fall between frame portions 12 and 14. The amount of force applied, or the extent to which the specimen is bent, or both, may be noted and the force exerted upon mandrel 95 is released.

As force upon knob 98 is reduced and the ram of the external mechanism is raised, springs 34 act upwardly against beam 80. Mandrel 95 is thereby raised to its original position, whereupon the apparatus 10 is ready for a next succeeding test.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. Apparatus for testing the ductility of a weld located within an elongated specimen, said apparatus for use with a device having a ram supported for raising and lowering over a bed, said apparatus comprising:
    a base defining an upper surface having a central opening;
    a pair of rollers, each of said rollers having a pair of ends and a width sufficient for supporting the specimen, each of said rollers further being supported at said ends by said base to extend over said opening;
    a beam;
    at least two upright supports mounted to said base to extend upwardly therefrom;
    said beam being fitted onto said upright supports to be freely vertically slidable thereon;
    stop means for preventing vertical upward movement of said beam on said upright supports beyond a predetermined height above said base;
    spring means connected between said base and said beam for biasing said beam upwardly against said stop means; and
    a downwardly extending mandrel connected to said beam, said mandrel defining at its lower end a working surface;
    said mandrel having a length and being located, when said beam is biased upwardly against said stop means, with said working surface above but between said rollers;
    whereby said base may be placed on the bed, the specimen may be positioned upon said rollers with the weld disposed equidistant between said rollers, said mandrel may be contacted by the ram for applying downward force by the ram, and whereby said mandrel may be forced downwardly by the ram to cause said mandrel to contact the specimen along said working surface to bend the specimen into said opening; and
    whereby upon subsequent upward movement of the ram, said spring means forces said beam upwardly against said stop means.

2. Apparatus as defined in claim 1, wherein each of said rollers is connected to said base by means for releasably connecting said roller.

3. Apparatus as defined in claim 2, further comprising additional pairs of rollers having a variety of diameters, and wherein said pair of rollers may be selectively interchanged with one of said additional pairs.

4. Apparatus as defined in claim 1, further comprising means for selectively moving said rollers of said pair toward and away from each other while supporting said rollers on said base.

5. Apparatus as defined in claim 4, wherein said means for selectively moving said rollers includes two pairs of members, each of said members disposed in parallel with the other member of said pair for sliding movement along said upper surface of said base, said pairs of members being disposed at opposite ends of said base, each of said rollers being connected at said roller ends between said members of each of said pairs of members, said selective moving means further including a pair of drawing means, each for drawing one of said pairs of members along said upper surface.

6. Apparatus as defined in claim 5, wherein each of said drawing means includes a block secured to said base, a screw shaft connected to said block for nonthreaded rotation, and a plate defining a threaded bore engaged with said screw shaft, said plate further being connected to one of said pairs of members, whereby rotation of said shaft causes sliding movement of said pair of members along said upper surface.

7. Apparatus as defined in claim 1, wherein said mandrel includes a mandrel body and a bottom portion attached thereto, said working surface being defined on said bottom portion.

8. Apparatus as defined in claim 7, wherein said working surface defines a curved, circular surface having a radius.

9. Apparatus as defined in claim 1, wherein said working surface is a roughened surface.

10. Apparatus as defined in claim 9, wherein said roughened surface is formed by knurling 11. Apparatus as defind in claim 9, wherein said roughened surface is defined by a plurality of pins embedded in said working surface.

* * * * *